United States Patent [19]

Lindquist et al.

[11] 4,362,762
[45] Dec. 7, 1982

[54] METHOD OF MAKING A WATER RESISTANT ORTHOPEDIC CAST

[75] Inventors: Julius A. Lindquist, Bridgewater; George J. Lukacs, Perth Amboy, both of N.J.

[73] Assignee: Johnson & Johnson Products, Inc., New Brunswick, N.J.

[21] Appl. No.: 268,942

[22] Filed: Jun. 1, 1981

[51] Int. Cl.$^3$ .................................................. C04B 11/16
[52] U.S. Cl. ...................................... 427/2; 128/91 R; 106/111
[58] Field of Search .......................... 128/91 R; 427/2; 106/111

[56] References Cited

U.S. PATENT DOCUMENTS 3,523,805  8/1970  Smith ................................ 128/91 R
4,136,687  1/1979  Dabroski .......................... 128/91 R

*Primary Examiner*—Sam Silverberg

[57] ABSTRACT

A method of improving the wet-strength characteristics of a plaster of Paris cast is disclosed. The cast bandage is immersed in dip water which contains 2%–15% by weight of a fluorochemical or the fluorochemical is applied to the finished cast. The fluorochemical is dispersed in the water by a nonionic or cationic surfactant. The resulting cast has improved water-resistant properties.

4 Claims, No Drawings

METHOD OF MAKING A WATER RESISTANT ORTHOPEDIC CAST

BACKGROUND OF THE INVENTION

The use of orthopedic bandages comprising plaster of Paris supported on a flexible material to immobilize the limb of a patient is well known in the art. Plaster of Paris has a known water sensitivity; therefore, patients wearing plaster of Paris casts must take care to avoid the rain and cannot shower. Because of this inconvenience, various improvements in the water resistance of plaster of Paris casts have been made. See, for example, U.S. Pat. Nos. 2,842,120 and 2,842,138 wherein melamine formaldehyde resin precursors have been added to plaster of Paris bandages to improve their water resistance.

Melamine formaldehyde resins have been known to cause allergic responses to the wearers of casts made from bandages of this type. Additionally, it is usually necessary to add the melamine formaldehyde precursors to the bandage in a separate step and, preferably, in an encapsulated form to preclude premature reaction. Various vinyl polymers such as polyvinyl pyrrolidone and polyvinyl acetate have also been added to improve the strength and water resistance of plaster of Paris casts (including the melamine formaldehyde resin—plaster of Paris casts noted above). See U.S. Pat. Nos. 3,671,280 and 3,649,319, respectively. Plaster of Paris casts of this type do show some improved water resistance and strength; however, further improvements in these properties would be desirable. Combinations of polyvinyl acetate and silicones have also been suggested in U.K. Pat. No. 859,018. The addition of a reactive silicone polymer to improved the water repellency of plaster of Paris casts is disclosed in U.S. Pat. No. 4,136,687.

The addition of a water-repellent or waterproofing agent to a cast bandage presents problems in both the manufacture of the bandage and the application of the bandage to a patient to form the cast. Plaster of Paris is the alphahemihydrate of $CaSO_4$. In the manufacture of the bandage, the plaster of Paris is mixed with a suitable binder such as casein, dextrin or polyvinyl acetate and applied to a gauze or other fabric substrate. The binder adheres the plaster particles on the substrate to prevent dry flake-off and wet slide-off of plaster. Prior to application of the bandage to a patient, a roll of the bandage is dipped into water to activate the plaster. The bandage is allowed to take up water which converts the calcium sulfate hemihydrate to the desired calcium sulfate dihydrate. The conversion to calcium sulfate dihydrate results in hardening of the cast.

The addition of a hydrophobic water-resistant agent to the cast bandage in the bandage manufacturing process interferes with the adhesion of the plaster of Paris particles to the fabric substrate. This can result in increased dry flake or dusting of the particles. The bandage could then have an insufficient plaster content to give the required rigidity to the finished cast.

The addition of a water-repellent material to a plaster of Paris bandage would also normally interfere with the setting of the plaster of Paris. When the plaster is moistened, it absorbs water and sets to a solid, rigid mass, calcium sulfate dihydrate. A water-repellent material could be expected to coat individual crystals or particles of the calcium sulfate hemihydrate and prevent water from contacting the crystals, thereby preventing the reaction which results in the formation of the solid calcium sulfate dihydrate. Thus, the process disclosed in U.S. Pat. No. 2,198,776 for manufacturing water-resistant wallboard would not be suitable for manufacturing cast bandages.

Fluorochemicals are known water-repellent agents. These materials have been in use for some time to impart water-repellent properties to textiles, paper, leather and other fibrous and porous material. In use, the fluorochemicals are applied to the material by coating or immersion and then cured by heat to obtain the water-repellent properties.

SUMMARY OF THE INVENTION

The present invention relates to a method of forming a water-repellent or water-resistant cast by the addition of a water-repellent fluorochemical to the cast bandage immediately prior to the application of the bandage to the patient to form the cast or immediately after the cast is applied. An emulsion of the fluorochemical is added to the dip water employed to activate the plaster of Paris or is applied to the cast after the cast has been formed on the patient. The cast bandage picks up a sufficient quantity of the fluorochemical from either form of application to give water-repellent or water-resistant characteristics to the finished cast.

Applicants have discovered that a number of fluorochemicals will give water-repellent properties to a cast without the necessity of heating the cast to cure the fluorochemical.

In the method of the present invention, an emulsion of a fluorochemical is added to the dip water used to activate the plaster of Paris of the bandage. The fluorochemical is added to the dip water in sufficient quantity to form a dispersion of the fluorochemical in the dip water of from 2% to 15% of the fluorochemical based on the weight of the dip water. The preferred amount of the fluorochemical in the dip water is from 4% to 6%. Increasing the amount of fluorochemical in the dip water to more than 15% results in a reduction of the dry-strength characteristics of the finished cast.

The water-repellent material of the present invention is an emulsion of a fluorochemical selected from the group consisting of:
(1) esters of the structure:

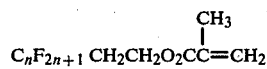

where n is an integer of from 3 to 14
(2) Polymers containing 3% to 25% by weight of a polymerizable monomer of the structure:

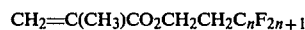

with a polymerizable vinyl compound selected from the group consisting of:

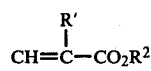

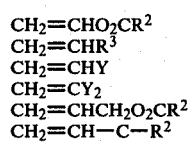

-continued

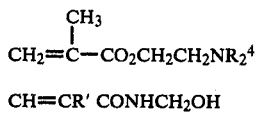

CH=CR' CONHCH₂OH wherein $R^1$ is H or methyl, $R^2$ is a saturated alkyl group containing from one to 18 carbons, $R^3$ is a phenyl or alkyl substituted phenyl, $R^4$ is hydrogen or saturated alkyl groups of one to six carbon and Y is fluorine, chlorine or bromine.

Methods of preparing the esters of paragraph 1 and the polymers of paragraph 2 are disclosed in U.S. Pat. No. 3,282,905.

(3) Polymers formed by the polymerization of monomers of the structure:

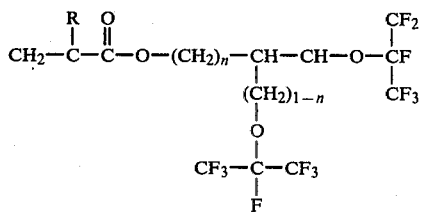

wherein R is H or CH₃, and n is zero or 1.

Methods of preparing such polymers are disclosed in U.S. Pat. No. 3,501,448; and (4) Fluorocarbon compounds of the formula:

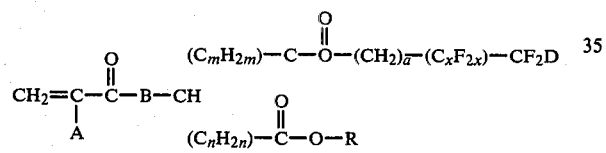

wherein R is selected from the group consisting of hydrogen, water-emulsifiable salt-forming cations and fluoroalkyl radicals of the formula $—(CH_2)_b—(C_yF_{2y})—CF_2E$, and wherein A is hydrogen or lower alkyl ($C_1$ to $C_5$), B is oxygen or NH, D and E are hydrogen or fluorine, m and n are integers from 0 to 4 inclusive, and totalling not more than 4, x and y are integers from 1 to 18 inclusive, and a and b are integers from 1 to 3 inclusive.

Methods of preparing such compounds are disclosed in U.S. Pat. No. 3,858,169.

The fluorochemicals are emulsified with a cationic or nonionic surfactant. An anionic surfactant cannot be used because anionic surfactants inhibit the setting of the plaster of Paris. As previously indicated, when the fluorochemicals of the present invention are added to the dip water used to activate the plaster of Paris, the amount of fluorochemical added to the dip water is from about 2% to about 15% based on the weight of the dip water. The fluorochemicals may also be applied to the cast after the cast bandage is applied to the patient. The fluorochemical is coated on the outer surface of the cast by brushing, spraying or application by wiping with a sponge or other absorbent. In applying the fluorochemical to a finished cast it is preferable to apply the fluorochemical to the cast immediately after the cast is formed. The fluorochemical is applied from an aqueous emulsion containing 2% to 15% by weight of the fluorochemical based on the total weight of the aqueous emulsion.

The effectiveness of a water-repellent material added to a cast bandage can be determined by measuring the wet crush strength of a cast. The wet crush strength of a cast system is determined by forming a cast on a two inch diameter dowel; allowing the cast to set; removing the dowel; aging the cast for a period of time, e.g., one to seven days, soaking the cast in water at 72° F. for two minutes; and, then crushing the cast on a Dillon Universal Tester. Another indication of the effectiveness of the water-repellant material is the determination of the amount of water taken up or retained by the cast after soaking the cast in water. This is determined by weighing the cast before and after soaking and is expressed as a percentage increase in the weight of the cast. The difference in the weight of the cast is attributed to the water that is retained by the cast after soaking.

The bead time, that is the length of time that a drop of water applied to the cast will be completely absorbed by the cast, is another test that may be used to determine relative water repellency.

In the examples, the setting time is determined by the following procedure. The cast bandage is dipped in water for five seconds. A cast is formed with five layers of the bandage. A No. 4 needle having a fixed weight of 300 grams is allowed to penetrate the cast. This is repeated every 15 seconds until the needle does not penetrate the cast. The elapsed time until the needle does not penetrate is considered to be the cast setting time.

EXAMPLE 1

Four individual commercially available plaster of Paris bandages, 4 inches×5 yards, were saturated in water, squeezed and wrapped on two-inch dowels. Three of the test cylinders were painted with a water diluted dispersion of a commercially available fluorochemical, a poly fluoryl acrylic polymer sold under the trademark "TLF" by duPont. This fluorochemical is the type disclosed in U.S. Pat. No. 3,282,905. The dispersion contained 15 grams fluorochemical/100 grams water and was applied at lapsed times of 5, 15 and 30 minutes after completion of wrapping. The fourth cylinder remained untreated to serve as the control for comparative purposes. Twenty-four hours after air drying, individual water droplets were applied to the surface of each test cylinder, and the time required for each drop to be absorbed was recorded to determine the bead time.

| Cylinder | Fluorochemical Application Timing | Bead Time |
|---|---|---|
| 1 | 5 min. | 11 min. |
| 2 | 15 min. | 14 min. |
| 3 | 30 min. | 8 min. |
| 4 | Control | 15 seconds |

EXAMPLE 2

Eight samples of commercially available plaster splints were soaked in 75° F. water, rubbed and set at room temperature. After air drying for 72 hours, each splint except a control was painted with various commercially available fluorochemical water-repellent emulsion dispersions of the type disclosed in U.S. Pat. No. 3,282,805. The solids content of the dispersions was from 20% to 30%. All test samples were air dried for seven days, then tested by placing individual water droplets on the surface of each test specimen and determining the time required for each droplet to be absorbed into the test specimen.

| Specimen | Bead Time |
|---|---|
| Control | 15 sec. |
| TLF 3580 | 120 min. |
| TLF 3475 | 16 min. |
| Zonyl NWJ | 80 min. |
| TLF 3195 | 60 min. |
| Zonyl NWJ (adj. pH 6.0) | 50 min. |
| Zepel RN | 10.5 min. |

Examples 1 and 2 show the significant increase in bead time or water absorption by the application of the fluorochemical to the cast without curing of the fluorochemical by heat.

EXAMPLE 3

The fluorochemical Zonyl NWJ was further tested by painting test cylinders at concentrations of 11% and 22% of the fluorochemical in water at 5 minutes after the test cylinders were formed with duplicate test cylinders painted 24 hours after forming the cylinders.

Test results given below illustrate the following.
(a) The dry strength of the cast remains unaffected.
(b) Water pickup of cylinders painted with fluorochemical on the outside surface absorb only about one-half as much as the control nonpainted casts. The phenomenon is attributed to repellency whereby only one surface allows ingress of water.
(c) When test cylinder ends were plugged with rubber stoppers, water pickup was reduced to very low values at which about 85% of dry crush strength was retained.
(d) The test method was expanded to include showering which simulates the force of rain droplets impinging on the cast surface. Via showering, water pickup exceeded the level at which plaster of Paris casts can undergo marked strength deterioration.

| Test Sample | Weight of Sample grams | Dry Crush lbs. | Water Pickup Immersion | Water Pickup Shower | Wet Crush lbs. |
|---|---|---|---|---|---|
| Control | 229 | 912 | — | — | — |
| Control | 225 | — | 14.3 | — | 433 |
| Control Plugged | 218 | — | 10.6 | — | 487 |
| Control | 219 | — | — | 11.5 | — |
| 11% Conc. (5 min.) Unplugged | — | 993 | — | — | — |
| 11% Conc. (5 min.) Unplugged | 244 | — | 6.5 | — | 563 |
| 11% Conc. (5 min.) Plugged | 220 | — | 1.8 | — | 835 |
| 11% Conc. (5 min.) Plugged | 222 | — | — | 8.9 | — |
| 11% Conc. (24 hours) Unplugged | 224 | 883 | — | — | — |
| 11% Conc. (24 hours) Unplugged | 238 | — | 7.8 | — | 543 |
| 11% Conc. (24 hours) Unplugged | 248 | — | 2.1 | — | 960 |
| 11% Conc. (24 hours) Plugged | 219 | — | — | 11.5 | — |
| 22% Conc. (5 min.) Unplugged | 229 | 917 | — | — | — |
| 22% Conc. (5 min.) Unplugged | 230 | — | 7.2 | — | 503 |
| 22% Conc. (5 min.) Plugged | 227 | — | 2.3 | — | 860 |
| 22% Conc. (5 min.) Plugged | 221 | — | — | 5.8 | — |
| 22% Conc. (24 hours) Unplugged | 248 | 993 | — | — | — |
| 22% Conc. (24 hours) Unplugged | 228 | — | 7.0 | — | 533 |
| 22% Conc. (24 hours) Plugged | 221 | — | 2.3 | — | 807 |

EXAMPLE 4

This study encompasses the addition of fluorochemical emulsion Zonyl NWJ to the dip water or soaking water for plaster bandage materials. Individual concentrations of 15%, 5.5% and 2.75% fluorochemical were utilized to obtain data on repellent effectiveness and affect on cast test cylinder crush strengths with respect to control non-treated test cylinders. All cylinders were air dried at 70° F. for seven days prior to testing.

| Test Sample | Weight grams | Dry Crush lbs. | Water Pickup Immersion | Water Pickup Shower | Wet Crush lbs. |
|---|---|---|---|---|---|
| Control | 235 | 900 | — | — | — |
| | 245 | — | 14.4 | — | 473 |
| | 236 | — | — | 12.0 | — |
| (15% Conc.) | 260 | 753 | — | — | — |
| | 272 | — | 0.52 | — | 630 |
| | 264 | — | — | 0.72 | — |
| (5.5% Conc.) | 270 | 863 | — | — | — |
| | 259 | — | 1.1 | — | 812 |
| | 268 | — | — | 1.3 | — |
| (2.75% Conc.) | 248 | 937 | — | — | — |
| | 251 | — | 4.2 | — | 816 |
| | 247 | — | — | 5.3 | — |

EXAMPLE 5

In the next series of experiments, commercially available fluorochemical emulsions were evaluated in the following manner;

A dip solution was prepared by diluting a commercial emulsion to 2.5% to 5% solids. A 4 inch×5 yard bandage was immersed in the dip solution, squeezed and wrapped around a two-inch dowel—after seven days drying a wet crush strength was measured, after a 2-minute water immersion.

Another bandage of the same type was prepared by immersion in water and wrapping on a two-inch dowel. After wrapping, the wet bandage was painted with the full strength emulsion. After 7 days drying, bead times and wet crush strength were measured on this cast also.

The results are tabulated in order of the wet crush strengths obtained.

| Name | Type | Strength | In Dip Water Wet Crush | In Dip Water Bead | Painted On Full Strength Wet Crush | Painted On Full Strength Bead |
|---|---|---|---|---|---|---|
| Zonyl-NWJ | Extended Fluorocarbon | 6.5% | 712 | 78 | 630 | 600+ |
| | | 5% | 865 | | | |
| | | 3.75% | 735 | 80 | | |
| | | 2.5% | 840 | | | |
| | | 1.25% | 625 | | | |
| TLF | Fluoro- | 5% | 670 | 145 | 563 | 464 |

-continued

| Name | Type | Strength | In Dip Water | | Painted On Full Strength | |
|---|---|---|---|---|---|---|
| | | | Wet Crush | Bead | Wet Crush | Bead |
| 2475 | polymer | 2½% | 642 | 40 | | |
| Zonyl NF | Fluoro-polymer | 5% | 652 | 896 | 647 | 562 |
| TLF | Fluoro-polymer | 5% | 598 | 316 | 750 | 91 |
| 4029B | polymer | 2½% | 633 | 115 | | |
| Zonyl NWK | Fluoro-polymer | 5% | 610 | 217 | | |
| | | 2½% | 560 | 28 | | |
| Zonyl NWG | Fluoro-polymer | 5% | 573 | 60 | 635 | 548 |
| | | 2½% | 528 | 16 | | |

EXAMPLE 6

Commercially available cast bandages with normal setting times of between 4 and 8 minutes (fast) and between 2 and 4 minutes (extra fast) were dipped in water containing fluorochemicals in the concentrations indicated in the table below. The set times given in the table indicate that the fluorochemical does not interfere with setting of the cast bandage.

| | | Set Time (Minutes) | |
|---|---|---|---|
| Additive | % In Dip Water | Fast Avg. | Extra Fast Avg. |
| Zonyl NWJ | 2.0 | 5.4 | 3.4 |

I claim:

1. A method of forming a water-resistant orthopedic cast comprising applying to the cast bandage, while the cast bandage is wet with water, a fluorochemical selected from the group consisting of:

(a) esters of the structure:

$$C_nF_{2n+1}CH_2CH_2O_2CC(CH_3)=CH_2$$

where n is an integer of from 3 to 14

(b) Polymers containing 3% to 25% by weight of a polymerizable monomer of the structure:

$$CH_2=C(CH_3)CO_2CH_2CH_2C_nF_{2n+1}$$

with a polymerizable vinyl compound selected from the group consisting of:

$$CH=C(R')-CO_2R^2$$
$$CH_2=CHO_2CR^2$$
$$CH_2=CHR^3$$
$$CH_2=CHY$$
$$CH_2=CY_2$$
$$CH_2=CHCH_2O_2CR^2$$
$$CH_2=CH-C-R^2$$
$$CH_2=C(CH_3)-CO_2CH_2CH_2NR_2^4$$
$$CH=CR'\ CONHCH_2OH$$

wherein $R^1$ is H or methyl, $R^2$ is a saturated alkyl group containing from one to 18 carbons, $R^3$ is a phenyl or alkyl substituted phenyl, $R^4$ is hydrogen or saturated alkyl groups of one to six carbon and Y is fluorine, chlorine or bromine:

(c) Polymers formed by the polymerization of monomers of the structure:

$$CH_2=C(R)-C(O)-O-(CH_2)_n-CH(-(CH_2)_{1-n}-O-C(CF_3)_2-F)-CH-O-CF(CF_2)(CF_3)$$

wherein R is H or $CH_3$, and n is zero or 1:

(d) Fluorocarbon compounds of the formula:

$$CH_2=C(A)-C(=O)-B-CH((C_mH_{2m})-C(=O)-O-(CH_2)_{\overline{a}}-(C_xF_{2x})-CF_2D)((C_nH_{2n})-C(=O)-O-R)$$

wherein R is selected from the group consisting of hydrogen, water-emulsifiable salt-forming cations and fluoroalkyl radicals of the formula $-(CH_2)_b-(C_yF_{2y})-CF_2E$, and wherein A is hydrogen or lower alkyl ($C_1$ to $C_5$), B is oxygen or NH, D and E are hydrogen or fluorine, m and n are integers from 0 to 4 inclusive, and totalling not more than 4, x and y are integers from 1 to 18 inclusive, and a and b are integers from 1 to 3 inclusive:

said fluorochemical being applied to said cast bandage as an aqueous dispersion containing from 2% to 30% by weight of said fluorochemical said aqueous dispersion containing a cationic or nonionic surfactant to maintain said fluorochemical in said dispersion, and allowing the cast to dry at room temperature.

2. The method of claim 1 in which the fluorochemical is applied to the cast bandage before the bandage is applied to the patient.

3. The method of claim 1 in which the fluorochemical is applied to the cast bandage after the cast bandage is applied to the patient.

4. The method of claim 2 in which the fluorochemical is added to the dip water in which the cast bandage is immersed, and the concentration of the fluorochemical is from 2% to 15% by weight.

* * * * *